United States Patent [19]

Quentin et al.

[11] Patent Number: 5,362,851
[45] Date of Patent: Nov. 8, 1994

[54] PEPTIDE SUBSTRATES, METHOD OF PREPARATION AND USE IN THE DETERMINATION OF PROTEIN C

[75] Inventors: Gérard Quentin, Colombes; Jean-Luc Martinoli, Villeneuve-la-Garenne, both of France

[73] Assignee: Serbio, Gennevilliers, France

[21] Appl. No.: 768,617

[22] PCT Filed: Dec. 31, 1990

[86] PCT No.: PCT/FR90/00973

§ 371 Date: Oct. 2, 1991

§ 102(e) Date: Oct. 2, 1991

[87] PCT Pub. No.: WO91/12268

PCT Pub. Date: Aug. 22, 1991

[30] Foreign Application Priority Data

Feb. 19, 1990 [FR] France ............... 90 01966

[51] Int. Cl.$^5$ .............. A61K 37/00; C07K 5/00; C07K 7/00; A01N 43/78
[52] U.S. Cl. ................. 530/331; 514/18; 514/365; 514/369; 435/23
[58] Field of Search ........... 530/331; 435/23; 514/18, 365, 369, 562, 560

[56] References Cited

U.S. PATENT DOCUMENTS 4,335,210 6/1982 Meister et al. ............ 435/113
4,508,644 4/1985 Heber et al. .
4,665,016 5/1987 Heber et al. .

FOREIGN PATENT DOCUMENTS 0004256 9/1979 European Pat. Off. .
0110306 6/1984 European Pat. Off. .
0280610 8/1988 European Pat. Off. .

Primary Examiner—Lester L. Lee
Assistant Examiner—A. M. Davenport
Attorney, Agent, or Firm—Burgess, Ryan and Wayne

[57] ABSTRACT

The present invention relates, by way of novel industrial products, to peptide compounds selected from the group consisting of
(i) the tripeptides of the formula $$Y-A_1-A_2-A_3-R \qquad (I)$$

in which
Y is H or an appropriate group blocking the N-terminal end,
$A_1$ is an amino acid residue selected from the group consisting of (2-oxothiazolidin-4-yl)carbonyl [abbreviated to THC], (2-oxotetrahydro-1,3-thiazin-5yl)carbonyl [abbreviated to TZC], thiazolidine-4-carbonyl [abbreviated to ATC] and (tetrahydro-1,3-thiazin-5-yl)carbonyl [abbreviated to AZC] residues,
$A_2$ is an amino acid residue selected from the group consisting of Pro, 3Hyp and 4Hyp residues, where the OH side-group of 3Hyp and 4Hyp is capable of being protected by an ether or ester protecting group,
$A_3$ is an amino acid residue selected from the group consisting of Arg and Lys residues, and
R is a labeling means; and
(ii) their addition salts.
These novel compounds are useful as substrates in the determination of Protein C.

3 Claims, No Drawings

PEPTIDE SUBSTRATES, METHOD OF PREPARATION AND USE IN THE DETERMINATION OF PROTEIN C

FIELD OF THE INVENTION

The present invention relates, by way of novel industrial products, to the peptide substrates of formula I below and their addition salts.

It further relates to the method of preparing these novel products and to their use in the field of the determination of Protein C.

PRIOR ART

It is known that a number of peptide substrates have already been proposed in the past for the identification and assay of numerous substances involved in the cascade mechanism of hemostasis.

It is known in particular that the substrate

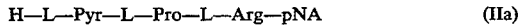

H—L—Pyr—L—Pro—L—Arg—pNA      (IIa)

[in which Pyr is the pyroglutaminyl residue (i.e. 5-oxoprolyl or pyrrolidin-2-one-5-carbonyl) and pNA is the p-nitroanilino radical], described in EP-A-0 004 256 as a chromogenic substrate for the determination of serine proteases and SH-proteases, has recently proved effective in the determination of Protein C.

It is also known that the substrate

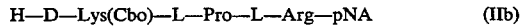

H—D—Lys(Cbo)—L—Pro—L—Arg—pNA      (IIb)

has already been used in the field of the determination of Protein C, but that its efficacy is inferior to that of the aforementioned compound IIa.

There is therefore a need for specific peptide substrates for the determination of Protein C. In fact, with the exception of the afore-mentioned substrates IIa and IIb, there are no other specific substrates for Protein C which are commercially available.

To meet this need, a novel technical solution is proposed, according to the invention, which uses peptide substrates having a different structure from that of the afore-mentioned products of formulae IIa and IIb known in the prior art.

SUMMARY OF THE INVENTION

According to a first feature of the invention, peptide substrates are provided, as novel industrial products, which are selected from the group consisting of (i) the tripeptides of the formula

Y—A₁—A₂—A₃—R      (I)

in which

Y is H or an appropriate group blocking the N-terminal end,

A₁ is an amino acid residue selected from the group consisting of (2-oxothiazolidin-4-yl)carbonyl [abbreviated to THC], (2-oxotetrahydro-1,3-thiazin-5-yl)carbonyl [abbreviated to TZC], thiazolidine-4-carbonyl [abbreviated to ATC] and (tetrahydro-1,3-thiazin-5-yl)carbonyl [abbreviated to AZC] residues, A₂ is an amino acid residue selected from the group consisting of Pro, 3Hyp and 4Hyp residues, where the OH side-group of 3Hyp and 4Hyp is capable of being protected by an ether or ester protecting group, A₃ is an amino acid residue selected from the group consisting of Arg and Lys residues, and R is a labeling means; and (ii) their addition salts.

According to a second feature of the invention, the tripeptide compounds of formula I and their addition salts are used for the determination of Protein C. To this end, a method of determination for the assay or identification of Protein C is provided which comprises bringing a tripeptide of formula I or one of its addition salts into contact with a body fluid (especially plasma, blood serum, or urine) or any other sample of natural or synthetic origin which may contain Protein C.

Finally, according to a third feature of the invention, a method of preparing the tripeptide compounds of formula I and their addition salts is provided.

ABBREVIATIONS

For convenience, the following abbreviations have been used in the present invention:

| the amino acid residues: | |
|---|---|
| Arg = | arginyl |
| ATC = | thiazolidine-4-carbonyl (or thioprolyl) |
| AZC = | (tetrahydro-1,3-thiazin-5-yl)carbonyl |
| 3Hyp = | 3-hydroxypropyl (or 3-hydroxypyrrolidine-2-carbonyl) |
| 4Hyp = | 4-hydroxypropyl (or 4-hydroxypyrrolidine-2-carbonyl) |
| Lys = | lysyl |
| Pro = | prolyl |
| Pyr = | pyroglutaminyl (or pyrrolidin-2-one-5-carbonyl) |
| THC = | 2-oxothiazolidin-4-yl)carbonyl |
| TZC = | (2-oxotetrahydro-1,3-thiazin-5-yl)carbonyl |
| the other abbreviations: | |
| Ac = | acetyl |
| AcOH = | acetic acid |
| Adoc = | adamantyloxycarbonyl |
| Aoc = | t-amyloxycarbonyl |
| Boc = | t-butoxycarbonyl |
| Bop = | (benzotriazol-1-yl)oxytris(dimethylamino)-phosphonium hexafluorophosphate (alternative nomenclature: CASTRO's reagent) of the formula |

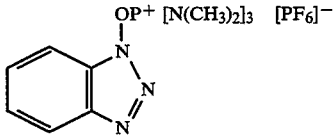

OP⁺ [N(CH₃)₂]₃ [PF₆]⁻

| Bu = | n-butyl |
| Bz = | benzoyl |
| Bzl = | benzyl |
| Cbo = | carbobenzoxy |
| o-Cl-pNA = | o-chloro-p-nitroanilino [or (2-Cl)pNA] |
| DCCI = | dicyclohexylcarbodiimide |
| DIEA = | diisopropylethylamine |
| DMF = | dimethylformamide |
| Et = | ethyl |
| Et₃N = | triethylamine |
| EtO = | ethoxy |
| Fmoc = | fluoren-9-ylmethoxycarbonyl |
| Foc = | furfuryloxycarbonyl |
| HMPT = | N,N,N',N',N'',N''-hexamethylphosphorotriamide |
| HOBT = | 1-hydroxybenzotriazole |
| HPLC = | high performance liquid chromatography |
| H-TFA = | trifluoroacetic acid (or HTFA) |
| Iboc = | isobornyloxycarbonyl |
| iPr = | isopropyl |
| Me = | methyl |
| MW = | molecular weight |
| OD = | optical density |
| Ph = | phenyl |

| | |
|---|---|
| pH = | cologarithm of the concentration of H+ ions |
| pNA = | p-nitroanilino [or (4-NO2)C6H4NH] |
| Pr = | n-propyl |
| RT = | room temperature (15–20° C.) |
| tBu = | t-butyl |
| THF = | tetrahydrofuran |
| TLC = | thin layer chromatography |
| Tos = | p-toluenesulfonyl (or tosyl) |
| Z = | benzyloxycarbonyl |
| Z(p-Cl) = | p-chlorobenzyloxycarbonyl |
| Z(p-OMe) = | p-methoxybenzyloxycarbonyl |

DETAILED DESCRIPTION OF THE INVENTION

In formula I above, the amino acid residue $A_1$ can be represented by the following structural formula:

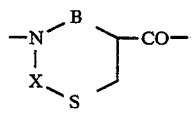
(III)

in which

B is a single bond or the group $CH_2$, and

X is $CH_2$ or CO.

When the pair (B;X) in formula III is (-;CO), ($CH_2$;CO), (-;$CH_2$) or ($CH_2$;$CH_2$), $A_1$ is respectively THC, TZC, ATC or AZC.

According to the invention, the amino acid residue $A_1$ will have the D or L configuration or else be a racemic mixture (DL) of these two configurations. $A_1$ will preferably be D-THC, D-TZC, D-ATC and D-AZC and more preferably L-THC, L-TZC, L-ATC and L-AZC. The amino acid residue $A_1$ which is considered to be the most valuable according to the invention is L-THC.

The hydrogen atom and radicals blocking the N-terminal end of peptides, such as those described in EP-A-0 110 306, U.S. application No. 4 480 030, FR-A-2 293 439 and U.S. application No. 4 440 678, may be mentioned among the groups Y which are suitable. The following may be indicated in particular among the groups Y, other than H, blocking said N-terminal end: $C_1$–$C_4$ alkyl groups (especially Me, Et, Pr, iPr, Bu, tBu), substituted or unsubstituted aryl groups (especially Ph, tolyl, xylyl, chlorophenyl, trifluoromethylphenyl, methoxyphenyl), substituted or unsubstituted aralkyl groups (especially Bzl, chlorobenzyl, dichlorobenzyl, trifluoromethylbenzyl, difluorobenzyl, methoxybenzyl, ethoxybenzyl, 3,4-methylenedioxybenzyl) and conventional protecting groups for the N-terminal end of peptides [especially Ac, Tos, Adoc, Aoc, Bz, Cbo, Fmoc, Foc, Iboc, Z, Z(p-Cl) and Z(p-OMe)].

The group Y other than H is introduced into the tripeptide of formula I in accordance with one of the following two reaction schemes:

scheme A

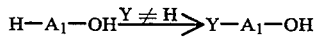

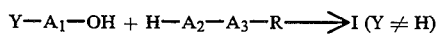

in which the OH group (of the carboxylic acid group) bonded to the CO-terminal end of $A_1$ is protected if appropriate; and scheme B

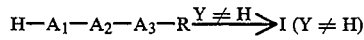

The choice of scheme A or B will depend on (i) the nature of the blocking group, and (ii) the labile character of the hydrogen atom of the N-terminal end which is located in the 3 position of the ring of $A_1$. With this in mind, scheme A will preferably be used when $A_1$ is THC or TZC.

Furthermore, as the rings of THC and AZC are generally obtained by cyclization at elevated temperature, the cyclization can be perturbed and/or the yields reduced by the presence of a group Y other than H, especially Y=alkyl, aryl or aralkyl, in the pyrolysis reaction mechanisms:

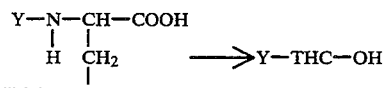

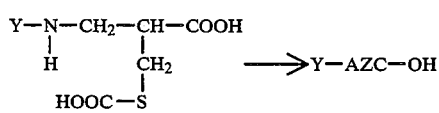

It is therefore advantageous to prepare the acids H-THC-OH and H-AZC-OH by pyrolysis and then to replace the H atom of the N-terminal end in accordance with the afore-mentioned scheme A to give the compounds of formula I in which Y is other than H.

The preferred group Y according to the invention is H. Briefly, the group Y=H will be replaced with a group Y other than H if and only if such a replacement substantially enhances the specificity of the substrate Y—$A_1$—$A_2$—$A_3$—R towards Protein C.

As indicated above, the OH side-group of 3Hyp and 4Hyp can be protected in the form of an ether or ester. The protecting group replacing the H atom of said OH group may be in particular a $C_1$–$C_4$ alkyl group (especially Me, Et, Pr, iPr, Bu, tBu), a substituted or unsubstituted aryl group (especially Ph, tolyl, xylyl, chlorophenyl, trifluoromethylphenyl, methoxyphenyl) or a substituted or unsubstituted aralkyl group (especially Bzl, chlorobenzyl, difluorobenzyl, trifluoromethylbenzyl, dichlorobenzyl, methoxybenzyl, ethoxybenzyl, 3,4-methylenedioxybenzyl), as envisaged in the definition of Y, in the context of protection in the form of an ether, or a $C_2$–$C_5$ aliphatic acyl group (especially Ac, propionyl, butanoyl, pentanoyl) or an aromatic group (especially Bz, toluoyl, chlorobenzoyl, methoxybenzoyl, 3,4-methylenedioxybenzoyl) in the context of protection in the form of an ester. If appropriate, said H atom may also be replaced with Tos or a trialkylsilyl group (especially trimethylsilyl or triethylsilyl) or the like.

Advantageously, the amino acid residues $A_2$ and $A_3$ will have the L configuration and the preferred groups for $A_2$ and $A_3$ according to the invention will be L-Pro, L-3Hyp and L-4Hyp and, respectively, L-Arg and L-Lys.

The labeling means R is well known in the art of biological and microbiological assays; reference is made in this connection to the prior art cited above and especially document U.S. Pat. No. 4,448,715. Said labeling means will preferably be selected from the group consisting of aminated groups NH-R' which (i) induce a color change, (ii) induce a change in fluorescence, or (iii) contain at least one radioactive element (for example an anilino or benzylamino group labeled with a $^{14}C$ or $^{3}H$ radioisotope). Any amino group NH-R' which gives, during or after the enzymic reaction, a signal capable of being amplified for detection (for example by measurement of the optical density at a given wavelength, or by measurement of the radioactivity) is suitable for the purposes of the invention. The amount of product H-R obtained by cleavage in the enzymic hydrolysis is proportional to the amount of enzyme used. Said amount of H-R can be determined by photometry, spectrophotometry, fluorospectrophotometry or electrochemistry.

The group R which is preferred according to the invention is a chromogenic group, typically a nitrophenylamino group (in which the phenyl radical is capable of being substituted by a group COOH, F, Cl, Br, $CH_3$, $OCH_3$, CN, $CF_3$ and/or $SO_3H$), or a fluorogenic group, typically a naphthylamino group (in which the naphthyl radical is capable of being substituted by a group $OCH_3$, COOH, $SO_3H$ or $CH_3$), and 4-methylcoumaryl-7-amino, 4-trifluoromethylcoumaryl-7-amino and analogous groups.

The following may be mentioned in particular among the chromogenic and fluorogenic aminated groups which are suitable according to the invention: p-nitroanilino (abbreviated to pNA), 2-carboxy-4-nitroanilino and 3-carboxy-4-nitroanilino, 2-halogeno-4-nitroanilino and 3-halogeno-4-nitroanilino (in which the halogen is F, Cl or Br), 2-methoxy-5-methyl-4-nitroanilino, 2-hydroxysulfonyl-4-nitroanilino, 4-trifluoromethyl-2-nitroanilino, 4-trifluoromethyl-3-nitroanilino, 4-cyano-2-nitroanilino, naphthyl-2-amino, 4-hydroxysulfonylnaphthyl-1-amino, quinolylamino, nitroquinolylamino and the like.

The preferred group R according to the invention is a chromogenic group, namely on the one hand pNA and on the other hand analogous groups in which the phenyl ring of pNA is substituted in the 2 or 3 position, said groups having the formula

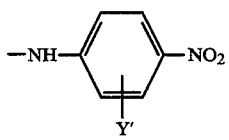
(VI)

in which Y' is Br, Cl, F, $CF_3$, COOH, COOW, $CONH_2$, CONHW, $CONW_2$, $CONH(CH_2)mNMe_2$, OH or OW, in which W is a $C_3-C_6$ alkyl, $C_6-C_{10}$ aryl, $C_7-C_{11}$ aralkyl or $C_3-C_8$ alicyclic group and m is an integer having a value of 1 to 10.

Such groups of formula VI in which the phenyl ring of the pNA group is substituted are described especially in document EP-A-0 110 306.

The addition salts according to the invention are essentially acid addition salts obtained by reacting a compound of formula I with a mineral or organic acid.

The best mode of carrying out the invention, which is recommended here, consists in using a substrate selected from the group consisting of (a) the tripeptide compounds of the formula $$H—A_1—A_2—A_3—pNA \qquad (I')$$

in which $A_1$ is D-THC, D-TZC, D-ATC, D-AZC, L-THC, L-TZC, L-ATC or L-AZC, $A_2$ is L-Pro, L-3Hyp or L-4Hyp and $A_3$ is L-Arg or L-Lys; and (b) their addition salts.

In this best mode of carrying out the invention, it is recommended more particularly to use L-TZC, L-ATC or, preferably, L-THC as the amino acid residue $A_1$.

For convenience, in the following description, an amino acid residue mentioned without the configuration (for example Pro) denotes, unless indicated otherwise, that said amino acid residue has the L configuration (i.e. L-Pro in the example in question).

Without in any way implying a limitation, a number of peptide compounds according to the invention have been collated in Table I below.

TABLE I

| Compound | 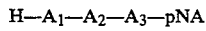H—$A_1$—$A_2$—$A_3$—pNA.HX | | | |
|---|---|---|---|---|
| | $A_1$ | $A_2$ | $A_3$ | HX |
| Ex. 1 | THC | Pro | Arg | H—TFA |
| Ex. 2 | THC | Pro | Arg | AcOH |
| Ex. 3 | THC | 3Hyp | Arg | AcOH |
| Ex. 4 | THC | 4Hyp | Arg | AcOH |
| Ex. 5 | THC | Pro | Lys | AcOH |
| Ex. 6 | TZC | Pro | Arg | AcOH |
| Ex. 7 | ATC | Pro | Arg | 2AcOH |
| Ex. 8 | AZC | Pro | Arg | 2AcOH |
| CP 1 (a) | Pyr | Pro | Arg | AcOH |
| CP 2 (b) | D-Lys(Cbo) | Pro | Arg | 2AcOH |

Notes
(a) reference product of formula IIa described in EP-A-0 004 256
(b) reference product of formula IIb The tripeptide compounds of formula I and their addition salts according to the invention can be prepared in accordance with a method known per se by the application of conventional reaction mechanisms of peptide synthesis. The method of preparation which is recommended here comprises reacting 1 mol of a dipeptide of the formula $$H—A_2—A_3—R \qquad (IV)$$

in which $A_2$, $A_3$ and R are defined as indicated above, with 1.0 to 1.3 mol of an amino acid of the formula $$Y—A_3—T \qquad (V)$$

in which Y and $A_3$ are defined as indicated above and T is OH, F, Cl or Br.

Advantageously, the reaction IV+V=I is carried out in an inert solvent, especially DMF or THF, at a temperature of between 0° and 50° C., especially at RT. Again advantageously, the reaction medium will comprise an excess of a base acting as a cosolvent and as a proton acceptor, such as $Et_3n$ or DIEA. When said reaction is carried out, a coupling agent, especially Bop or HOBT, will also be incorporated into said reaction medium, in particular when T is OH. When HOBT is used as the coupling agent, an appropriate amount of DCCI will advantageously be associated with said agent.

In practice, molar ratios IV/$Et_3N$ or IV/DIEA of ½ to ¼ will be used and, when T=OH, molar ratios IV/HOBT or IV/Bop of 1/1 to ½ will be used; when DCCI is used, the molar ratio IV/DCCI will be of the order of 1/1.5-½. The purpose of the coupling agents HOBT and Bop is to activate the carboxylic acid group, COOH, of the CO-terminal end (when T=OH) and they have the advantage of not causing racemization. The agent Bop will be used at a pH of 7-8 and the agent HOBT at a pH of 5 to 8. With regard to its coupling properties, Bop will be preferred to HOBT. The tripeptide of formula I is isolated from the reaction medium of the reaction IV+V=I in accordance with the following steps:

evaporation of the inert solvent to dryness under vacuum, precipitation of the resulting evaporation residue with ether (MeOMe or EtOEt), followed by recovery of the precipitate by filtration, taking-up of the filtered precipitate in the minimum amount of a $CHCl_3/MeOH/AcOH$ mixture, chromatography of the resulting mixture using said solvent $CHCl_3/MeOH/AcOH$, and pooling of the homogeneous fractions resulting from said chromatography, and evaporation of said solvent.

The tripeptide compounds of formula I and their addition salts constitute specific substrates for Protein C. In the recommended method of determining Protein C, a given amount of a tripeptide of formula I or of one of its addition salts (at a concentration of the order of 10 mg/ml) is brought into contact, in an appropriate aqueous liquid medium such as a buffered isotonic solution, with a test sample (diluted if appropriate) which may contain Protein C, for at least 0.5 h at a temperature of between RT and 40° C., especially 37° C.

The activity of the tripeptides according to the invention towards Protein C was determined by one of the conventional methods, such as the one described in publication EP-A-0 280 160 (see page 14), the hydrolysis rate being assessed by the variation in optical density with time ($\Delta OD/min$). The results obtained with equimolar doses have been collated in Table II below, where the activity of the reference product of formula IIa is specified as being equal to 100% for the sake of convenience.

TABLE II

| ACTIVITY TOWARDS PROTEIN C | |
|---|---|
| Product | Activity |
| Ex. 1 | 148% |
| Ex. 2 | 153% |
| Ex. 3 | 118% |
| Ex. 4 | 111% |
| Ex. 5 | 122% |
| Ex. 6 | 105% |
| Ex. 7 | 110% |
| Ex. 8 | 103% |
| CP 1 | 100% |
| CP 2 | 34% |

The comparative results in Table II show that the tripeptides according to the invention are at least as active as the reference product CP 1.

An assay kit for the determination of Protein C, which contains a tripeptide of formula I or one of its addition salts and, if appropriate, a standard sample of Protein C (of human or bovine origin) and of buffered dilution media, is also provided according to the invention.

Further advantages and characteristics of the invention will be understood more clearly from the following description of Preparatory Examples. These data do not in any way imply a limitation and are given by way of illustration.

PREPARATION I

Preparation of L-THC-L-Pro-L-Arg-pNA.H-TFA (Example 1)

a) Z-L-Arg-pNA.HCl 3.44 g (0.01 mol) of Z-L-Arg-OH.HCl are dissolved in 20 ml of anhydrous HMPT at RT and 1.39 ml (0.01 mol) of $Et_3n$ are then added at RT, with stirring. 2.46 g (0.015 mol) of p-nitrophenyl isocyanate are added to the resulting solution. The resulting reaction medium is stirred for 24 h at RT and then evaporated under vacuum and the residue is taken up with the minimum amount of AcOH and then diluted with AcOEt. The resulting solution is subsequently extracted successively three times with small amounts of 0.5 M $NaHCO_3$, three times with a solution of $KHSO_4$ at 50 g/l and then several times with $H_2O$ semisaturated with NaCl. The organic phase is then dried over anhydrous sodium sulfate. After filtration (removal of $Na_2SO_4$), the solvent is evaporated off and the evaporation residue is recrystallized from an AcOEt/MeOMe mixture (3/7 v/v) to give 3.5 g of the expected product in the form of a white powder. M.p.=128°-130° C.

Analysis (TLC on silica gel):

Rf=0.5 in AcOEt/pyridine/AcOH/$H_2O$ (20/4.5/3/1 v/v);

Rf=0.69 in $CHCl_3/MeOH/AcOH$ (5/3/1 v/v).

b) H-L-Arg-pNA,2HBr 1 g (2.15 mmol) of Z-L-Arg-pNA.HCl is charged into a glass/Teflon apparatus. 8 ml of glacial AcOH, 2 ml of anisole and 10 ml of a solution of HBr (at 33% w/v) in AcOH are added successively under an inert atmosphere (stream of nitrogen). The reaction is left to proceed for 1 h at RT under a nitrogen atmosphere. After this time has elapsed, the reaction mixture, which has become homogeneous during the deprotection, is precipitated in ether (MeOMe or EtOEt). After decantation, the supernatant is discarded and the precipitate is washed several times with ether. The precipitate is collected by filtration and dried under vacuum over KOH for 24 h to give 0.95 g of the expected product.

Analysis (TLC on silica gel):

Rf=0.04 in AcOEt/pyridine/AcOH/$H_2O$ (20/4.5/3/1.5 v/v);

Rf=0.38 in BuOH/AcOH/$H_2O$ (3/1/1 v/v).

c) BOC-L-Pro-L-Arg-pNA.HBr 1 g (2.19 mmol) of H-L-Arg-pNA.2HBr is dissolved in 10 ml of DMF, and 0.854 ml (6.57 mmol) of DIEA is then added. In another vessel, a solution of 4.71 mg (2.19 mmol) of Boc-L-Pro-OH in 50 ml of DMF is neutralized with 0.285 ml of DIEA. The two solutions are mixed and 970 mg of Bop are then added while the resulting mixture is kept at RT, with stirring, the pH being kept at between 7.0 and 8.0 throughout the reaction by the addition of small portions of DIEA. After one hour, the reaction is complete and the reaction mixture is evaporated to dryness under vacuum; the evaporation residue is taken up with an AcOEt/MeOH mixture and extracted with a 0.5 M aqueous solution of $NaHCO_3$. The organic phase is dried over sodium sulfate, concentrated and precipitated in ether (MeOMe or EtOEt) to give 877 mg (yield: 70%) of the expected product.

Analysis (TLC on silica gel):

Rf=0.27 in $CHCl_3/MeOH/AcOH$ (20/3/1 v/v);

Rf=0.71 in $CHCl_3/MeOH/AcOH$ (10/3/1 v/v).

d) H-L-Pro-L-Arg-pNA.2H-TFA 850 mg (1,485 mmol) of Boc-L-Pro-L-Arg-pNA.HBr and then 6 ml of $CH_2Cl_2$ and 6 ml of H-TFA are introduced successively into a reactor. After a reaction time of 0.25 h, the reaction mixture is precipitated directly in ether. After drying of the resulting precipitate, 837 mg of the expected product are obtained.

Analysis (TLC on silica gel):
Rf=0.56 in BuOH/AcOH/$H_2O$ (3/1/1 v/v);
Rf=0.13 in $CHCl_3$/MeOH/AcOH (5/3/1 v/v).

e) L-THC-L-Pro-L-Arg-pNA.H-TFA

Following the operating protocol described in section c) above, a reaction mixture comprising (i) 800 mg (1.3 mmol) of H-L-Pro-L-Arg-pNA.2H-TFA, (ii) 190 mg (1.3 mmol) of H-THC-OH, (iii) 1 ml of DIEA and (iv) 5.75 mg (1.3 mmol) of Bop is reacted in DMF at RT for 1.5 h, with stirring. The reaction mixture is subsequently evaporated under vacuum and the residue is then precipitated in EtOEt. The white precipitate obtained is taken up in the minimum amount of the solvent system $CHCl_3$/MeOH/AcOH (5/3/1 v/v) and chromatographed on silica gel using the same solvent system. The homogeneous fractions are recovered, pooled and evaporated to give 410 mg (yield: 54%) of the expected product.

Analysis (TLC on silica gel):
Rf=0.23 in $CHCl_3$/MeOH/AcOH (10/3/1 v/v);
Rf=0.33 in $CHCl_3$/MeOH/AcOH (5/3/1 v/v).

PREPARATION II

Preparation of L-THC-L-Pro-L-Arg-pNA.AcOH (Example 2)

Starting from L-THC-L-Pro-L-Arg-pNA.H-TFA obtained according to Preparation I, the product of Example 2, namely L-THC-L-Pro-L-Arg-pNA.AcOH, is prepared by ion exchange on AMBERLITE ® IRA 401 S resin (acetylated beforehand), the eluent being an MeOH/$H_2O$ mixture (3/2 v/v).

PREPARATION III

The product of Example 1 is prepared, the chromatography on silica gel in step Ie being replaced with HPLC (HYPERSIL ® C 18 column of particle size 3 micrometers). The product obtained is purer than that obtained in Preparation I.

What is claimed is:

1. A tripeptide compound of the formula

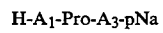

wherein $A_1$ is 2-(oxathiazolidin-4-yl)carbonyl (THC), and $A_3$ is Arg or Lys, and acid addition salts thereof.

2. A tripeptide compound according to claim 1 wherein (i) $A_1$ has the L- or D- configuration, and (ii) Pro and $A_3$ have the L-configuration.

3. A peptide compound according to claim 2 which is selected from the group consisting of H-L-THC-L-Pro-L-Arg-pNA and its addition salts.

* * * * *